(12) United States Patent
Reuter et al.

(10) Patent No.: US 6,774,246 B2
(45) Date of Patent: Aug. 10, 2004

(54) METHOD FOR PRODUCING PHTHALIC ANHYDRIDE

(75) Inventors: Peter Reuter, Mannheim (DE); Guido Voit, Freinsheim (DE); Thomas Heidemann, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/344,517

(22) PCT Filed: Aug. 20, 2001

(86) PCT No.: PCT/EP01/09584

§ 371 (c)(1),
(2), (4) Date: Feb. 12, 2003

(87) PCT Pub. No.: WO02/16299

PCT Pub. Date: Feb. 28, 2002

(65) Prior Publication Data

US 2003/0181735 A1 Sep. 25, 2003

(30) Foreign Application Priority Data

Aug. 21, 2000 (DE) .......................................... 100 40 827

(51) Int. Cl.⁷ ............................................. C07D 307/89
(52) U.S. Cl. ....................................................... 549/248
(58) Field of Search ........................................ 549/248

(56) References Cited

U.S. PATENT DOCUMENTS

| | | |
|---|---|---|
| 4,077,984 A | 3/1978 | Blechschmitt et al. |
| 4,203,906 A | 5/1980 | Takada et al. |
| 4,284,571 A | 8/1981 | Sato et al. |
| 4,286,101 A | 8/1981 | Hashizume et al. |
| 5,225,574 A | 7/1993 | Aichinger et al. |
| 5,998,572 A | 12/1999 | Rostami et al. |
| 6,288,273 B1 | 9/2001 | Heidemann et al. |
| 6,380,399 B1 * | 4/2002 | Okuno et al. ............... 549/250 |

FOREIGN PATENT DOCUMENTS

| | | |
|---|---|---|
| EP | 163 231 | 12/1985 |
| EP | 286 448 | 10/1988 |
| EP | 1 063 222 | 12/2000 |

OTHER PUBLICATIONS

Dewent Abst DE 4109387–A.

* cited by examiner

*Primary Examiner*—Fiona T. Powers
(74) *Attorney, Agent, or Firm*—Keil & Weinkauf

(57) ABSTRACT

A process for preparing phthalic anhydride by gas-phase oxidation of xylene, naphthalene or mixtures thereof over two different fixed-bed catalysts arranged in zones in a shell-and-tube reactor which is thermostated by means of a heat transfer medium is carried out so that the maximum temperature in the second catalyst zone in the flow direction is at least 52° C. lower than the maximum temperature in the first catalyst zone.

The process of the present invention makes it possible to prepare phthalic anhydride in high yields under conditions relevant to industrial practice.

11 Claims, No Drawings

METHOD FOR PRODUCING PHTHALIC ANHYDRIDE

The present invention relates to a process for preparing phthalic anhydride by gas-phase oxidation of xylene, naphthalene or mixtures thereof over two different fixed-bed catalysts arranged in zones in a shell-and-tube reactor which is thermostated by means of a heat transfer medium.

It is known that phthalic anhydride is prepared industrially by catalytic gas-phase oxidation of o-xylene or naphthalene in shell-and-tube reactors. The starting material is a mixture of a gas comprising molecular oxygen, for example air, and the o-xylene and/or naphthalene to be oxidized. The mixture is passed through a large number of tubes located in a reactor (shell-and-tube reactor), with each of the tubes containing a bed of at least one catalyst. To regulate the temperature, the tubes are surrounded by a heat transfer medium, for example a salt melt. Nevertheless, local temperature maxima (hot spots) in which the temperature is higher than in the remainder of the catalyst bed can occur. These hot spots give rise to secondary reactions such as total combustion of the starting material or lead to the formation of undesirable by-products which can be separated from the reaction product only with difficulty, if at all. Furthermore, the catalyst can be irreversibly damaged above a particular hot spot temperature.

The hot spot temperatures are usually in a temperature range from 400 to 500° C., in particular from 410 to 460° C. Hot spot temperatures above 500° C. lead to a severe decrease in the achievable PA yield and in the operating life of the catalyst. On the other hand, hot spot temperatures which are too low lead to an excessively high content of under-oxidation products in the phthalic anhydride (in particular phthalide), resulting in a significant deterioration in the product quality. The hot spot temperature depends on the xylene loading of the air stream, on the space velocity of the xylene/air mixture over the catalyst, on the state of aging of the catalyst, on the heat transfer conditions in the fixed-bed reactor (reactor tube, salt bath) and on the salt bath temperature.

To reduce this hot spot, various measures have been proposed in, for example, DE 25 46 268 A, EP 286 448 A, DE 29 48 163 A, EP 163 231 A, DE 41 09 387 A, WO 98/37967 and DE 198 23 362 A. In particular, as described in DE 40 13 051 A, a change has been made to arranging catalysts of differing activity in zones in the catalyst bed, with the less active catalyst generally being located closer to the gas inlet and the more active catalyst being located closer to the gas outlet. The process is carried out using a two-stage salt bath, with the salt bath temperature of the first reaction zone in the flow direction of the reaction mixture being kept 2–20° C. higher than the salt bath temperature of the second reaction zone. The catalyst volume in the first reaction zone is from 30 to 75% by volume and that in the second reaction zone is from 25 to 70% by volume. The temperature of the hot spot in the first reaction zone is higher than that in the second reaction zone. The difference between the hot spot temperatures in the modes of operation described in the examples is considerably less than 50° C.

DE 28 30 765 A describes a shell-and-tube reactor in which a catalyst is present in two reaction zones and which is suitable for, inter alia, the preparation of phthalic anhydride. The reaction temperature in the second reaction zone from the gas inlet is higher than that in the first reaction zone.

DE 29 48 163 A describes a process for preparing phthalic anhydride using two different catalysts arranged in zones, with the catalyst of the first zone making up from 30 to 70% of the total length of the catalyst bed and the catalyst of the second zone making up from 70 to 30% of the total length of the catalyst bed. This is said to reduce the temperature of the hot spot. However, it has been found that the yield of phthalic anhydride even at the low o-xylene loadings in the starting gas mixture (maximum 85 g/standard m$^3$) employed in this publication leaves something to be desired. A similar process is disclosed in DE 30 45 624 A.

DE 198 23 262 describes a process for preparing phthalic anhydride using at least three coated catalysts arranged one above the other in zones, with the catalyst activity increasing from zone to zone from the gas inlet end to the gas outlet end. In this process, the difference in the hot spot temperature from catalyst to catalyst is not more than 10° C.

It is an object of the present invention to provide a process for preparing phthalic anhydride which gives high yields of phthalic anhydride even at high o-xylene or naphthalene loadings and at high space velocities.

We have found that this object is achieved by carrying out the preparation of phthalic anhydride over two catalysts having differing activities and arranged in zones and controlling the process in such a way that the hot spot temperature in the catalyst zone furthest from the gas inlet (in the flow direction) is at least 52° C. lower than that in the catalyst zone closest to the gas inlet.

The present invention accordingly provides a process for preparing phthalic anhydride by gas-phase oxidation of xylene, naphthalene or mixtures thereof over two different fixed-bed catalysts arranged in zones in a shell-and-tube reactor which is thermostated by means of a heat transfer medium, wherein the maximum temperature (hot spot temperature, i.e. localized region of highest temperature in a catalyst zone) in the second catalyst zone furthest from the gas inlet is at least 52° C. lower than the maximum temperature in the first catalyst zone.

The maximum temperature in the second catalyst zone is preferably at least 55° C., in particular at least 60° C., lower than the maximum temperature in the first catalyst zone. However, the reaction is generally controlled so that the maximum temperature in the first catalyst zone is not more than 75° C., in particular not more than 70° C., higher than that in the second catalyst zone. The temperature difference is thus preferably in the range from 52 to 75° C.

Furthermore, the process is carried out so that the hot spot temperature in the first catalyst zone is less than 470° C., preferably less than 450° C.

The difference in the hot spot temperatures can be adjusted in various ways. For example, it can be done by increasing the admission pressure of the starting gas mixture by up to 10% or by lowering the amount of air used for the oxidation by up to 20%. However, the temperature difference is preferably controlled by means of the bed length ratio of the two catalysts or by means of the temperature of the heat transfer medium (hereinafter, reference will always be made to the preferred heat transfer medium, namely a salt bath), in particular when the two catalyst zones are thermostated by means of different salt bath circuits. The bed length of the first catalyst zone preferably makes up more than 60%, in particular more than 70% and particularly preferably more than 75%, of the total height of the catalyst bed in the reactor tube.

If the salt bath temperature is used for control, an increase in the salt bath temperature leads to an increase in the hot spot temperature in the first catalyst zone and to a decrease in the second catalyst zone. For this reason, a slight increase or decrease, e.g. by 1, 2 or 3° C., is generally sufficient to set the desired hot spot temperature difference. If the two catalyst zones are thermostated by means of different salt bath circuits, the upper salt bath circuit, i.e. the salt bath circuit which thermostats the first catalyst zone, is preferably operated at a temperature which is 1–5° C. higher than that of the lower salt bath circuit. Alternatively, the temperature of the salt bath which thermostats the second catalyst zone is decreased by up to 20° C.

The operating life of the catalyst is generally from about 4 to 5 years. The activity of the catalyst generally decreases somewhat over the course of time. As a result, the hot spot temperature difference can drop below the minimum value of 52° C. It can then be restored to a value above 52° C. by increasing the salt bath temperature as described above. The process is preferably carried out so that the hot spot temperature difference is maintained for at least the first 50%, in particular at least the first 70%, particularly preferably at least the first 90%, of the operating life of the catalyst and particularly advantageously during essentially the entire operating life of the catalyst.

The hot spot temperature is determined in a known manner, e.g. by installation of a plurality of thermocouples in the reactor.

Supported oxidic catalysts are suitable as catalysts. In the preparation of phthalic anhydride by gas-phase oxidation of o-xylene or naphthalene, use is made of spherical, ring-shaped or dish-shaped supports comprising a silicate, silicon carbide, porcelain, aluminum oxide, magnesium oxide, tin dioxide, rutile, aluminum silicate, magnesium silicate (steatite), zirconium silicate or cerium silicate or mixtures thereof. Catalytically active constituents are generally titanium dioxide, particularly in the form of its anatase modification, together with vanadium pentoxide. In addition, the catalytically active composition may further comprise small amounts of many other oxidic compounds which act as promoters to influence the activity and selectivity of the catalyst, for example by reducing or increasing its activity. Examples of such promoters are alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. The alkali metal oxides act, for example, as promoters which reduce the activity and increase the selectivity, while oxidic phosphorus compounds, in particular phosphorus pentoxide, increase the activity of the catalyst but reduce its selectivity. Catalysts which can be used are described, for example, in DE 25 10 994, DE 25 47 624, DE 29 14 683, DE 25 46 267, DE 40 13 051, WO 98/37965 and WO 98/37967. Coated catalysts in which the catalytically active composition is applied in the form of a shell to the support (cf., for example, DE 16 42 938 A, DE 17 69 998 A and WO 98/37967) have been found to be particularly useful.

The less active catalyst is arranged in the fixed bed so that the reaction gas comes into contact with this catalyst first and only then comes into contact with the more active catalyst in the second zone. The catalysts having differing activities can be thermostated to the same temperature or to different temperatures. In general, a catalyst doped with alkali metal oxides is used in the first catalyst zone closest to the gas inlet and a catalyst doped with smaller amounts of alkali metal oxides and/or phosphorus compounds and/or further promoters is used in the second reaction zone.

Particular preference is given to catalysts having the following composition:

for the first zone:
   from 3 to 5% by weight of vanadium pentoxide
   from 0.1 to 1% by weight of an alkali metal oxide, e.g. cesium oxide
   from 94 to 96.9% by weight of titanium dioxide for the second zone:
   from 6 to 9% by weight of vanadium pentoxide
   from 0 to 0.3% by weight of an alkali metal oxide, e.g. cesium oxide
   from 0.05 to 0.4% by weight of phosphorus pentoxide (calculated as P)
   if desired, from 1 to 5% by weight of a further promoter, in particular $Sb_2O_3$
   from 85.3 to 93.95% by weight of titanium dioxide In general, the reaction is carried out in such a way that the major part of the o-xylene and/or naphthalene present in the reaction gas is reacted in the first reaction zone.

For the reaction, the catalysts are introduced into the tubes of a shell-and-tube reactor so as to form adjacent zones. The reaction gas is passed over the catalyst bed prepared in this way at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, and at a space velocity of generally from 750 to 5000 $h^{-1}$, preferably from 2000 to 5000 $h^{-1}$. The reaction gas (starting gas mixture) fed to the catalyst is generally produced by mixing a gas which comprises molecular oxygen and may further comprise suitable reaction moderators and/or diluents such as steam, carbon dioxide and/or nitrogen, with the o-xylene or naphthalene to be oxidized. The reaction gas generally contains from 1 to 100 mol %, preferably from 2 to 50 mol % and particularly preferably from 10 to 30 mol %, of oxygen. In general, the reaction gas is laden with from 5 to 140 g of o-xylene and/or naphthalene per standard $m^3$ of gas, preferably from 60 to 120 g of o-xylene and/or naphthalene per standard $m^3$ of gas and particularly preferably from 80 to 120 g of o-xylene and/or naphthalene per standard $m^3$ of gas.

If desired, a downstream finishing reactor, as described, for example, in DE 198 07 018 or DE 20 05 969 A, can be additionally provided for the preparation of phthalic anhydride. As catalyst for this finishing reactor, preference is given to using a catalyst which is even more active than the catalyst of the second zone. In particular, this catalyst has the following composition:

from 6 to 9% by weight of vanadium pentoxide
   from 1 to 5% by weight of an activity-increasing promoter, in particular $Sb_2O_3$
   from 0.1 to 0.5% by weight of phosphorus pentoxide (calculated as P)
   from 85.5 to 92.9% by weight of titanium dioxide.

The process of the present invention has the advantage that phthalic anhydride can be prepared in high yield and with low concentrations of by-products, in particular phthalide, even at high loadings of o-xylene and/or naphthalene and at high space velocities. Under the conditions of the process of the present invention, the phthalide concentration is no higher than 0.1% by weight, based on PA. The advantages of the process of the present invention are particularly evident when the activity of the catalyst system used decreases due to aging. Even after a long period of operation, there is only an insignificant increase in the hot spot in the second catalyst zone.

The temperature control used according to the present invention can also be employed in the preparation of other products by catalytic gas-phase oxidation, e.g. acrylic acid (from propene), maleic anhydride (from benzene, butene or butadiene), pyromellitic anhydride (from durene), benzoic acid (from toluene), isophthalic acid (from m-xylene), terephthalic acid (from p-xylene), acrolein (from propene), methacrylic acid (from isobutene), naphthoquinone (from naphthalene), anthraquinone (from anthracene), acrylonitrile (from propene) and methacrylonitrile (from isobutene).

The following examples illustrate the invention without restricting its scope.

EXAMPLES

1) Production of the Catalysts I–III

Catalyst I:

50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 20 $m^2/g$, 2.19 kg of vanadyl oxalate, 0.176 kg of cesium sulfate, 44.1 kg of water and 9.14 kg of formamide until the weight of the applied layer was 10.5% of the total weight of the finished catalyst (after calcination at 450° C.).

The catalytically active composition applied in this way, i.e. the catalyst shell, comprised 4.0% by weight of vanadium (calculated as $V_2O_5$), 0.4% by weight of cesium (calculated as Cs) and 95.6% by weight of titanium dioxide.

Catalyst II 50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 20 $m^2/g$, 4.11 kg of vanadyl oxalate, 1.03 kg of antimony trioxide, 0.179 kg of ammonium dihydrogen phosphate, 0.045 kg of cesium sulfate, 44.1 kg of water and 9.14 kg of formamide until the weight of the applied layer was 10.5% of the total weight of the finished catalyst (after calcination at 450° C.).

The catalytically active composition applied in this way, i.e. the catalyst shell, comprised 0.15% by weight of phosphorus (calculated as P), 7.5% by weight of vanadium (calculated as $V_2O_5$), 3.2% by weight of antimony (calculated as $Sb_2O_3$), 0.1% by weight of cesium (calculated as Cs) and 89.05% by weight of titanium dioxide.

Catalyst III 50 kg of steatite (magnesium silicate) rings having an external diameter of 8 mm, a length of 6 mm and a wall thickness of 1.5 mm were heated to 160° C. in a coating drum and sprayed with a suspension comprising 28.6 kg of anatase having a BET surface area of 11 $m^2/g$, 3.84 kg of vanadyl oxalate, 0.80 kg of antimony trioxide, 0.239 kg of ammonium dihydrogen phosphate, 44.1 kg of water and 9.14 kg of formamide until the weight of the applied layer was 12.5% of the total weight of the finished catalyst (after calcination at 450° C.).

The catalytically active composition applied in this way, i.e. the catalyst shell, comprised 0.2% by weight of phosphorus (calculated as P), 7.0% by weight of vanadium (calculated as $V_2O_5$), 2.5% by weight of antimony (calculated as $Sb_2O_3$) and 90.3% by weight of titanium dioxide.

2) Oxidation of O-Xylene

2a) Preparation of PA—According to the Present Invention and Comparison (Setting of the Hot Spot Temperature Difference by Variation of Bed Length)

In a 10 l tube reactor (99 normal tubes and 2 thermocouple tubes), firstly (at the bottom) catalyst II (comparison: 1.30 m; according to the present invention: 0.70 m) and subsequently catalyst I (comparison: 1.70 m; according to the present invention: 2.30 m) were in each case placed in each of the 3.60 m long iron tubes having an internal diameter of 25 mm (thermocouple tubes 29 mm with thermocouple sheath of 10 mm internal diameter and 30 installed thermocouples (every 10 cm)). By means of pressure balancing, it was ensured that the same inlet pressure prevailed at each tube inlet. If necessary, a little catalyst I was added or removed to/from the 99 normal tubes; in the case of the 2 thermocouple tubes, pressure balancing was achieved by addition of inert material in the form of steatite spheres or quartz spheres. To regulate the temperature of the iron tubes, they were surrounded by a salt melt which was located in two separate salt baths. The lower salt bath surrounded the tubes from the lower tube plate to a height of 1.30 m, and the upper salt bath surrounded the tubes from the height of 1.30 m to the upper tube plate. 4.0 standard $m^3/h$ per tube of air laden with 100 g of 98.5% strength by weight of o-xylene per standard $m^3$ of air were passed through the tubes from the bottom upward (after a running-up time of about two months). After leaving the main reactor, the crude product gas stream was cooled to 280–290° C. and passed through an adiabatic finishing reactor (internal diameter: 0.45 m, height: 0.99 m) charged with 100 kg of catalyst III.

The data listed in the following table were obtained in these experiments (day=day of operation starting from the first start-up of the catalyst; SBT top=salt bath temperature of the salt bath nearest the reactor inlet; SBT bottom=salt bath temperature of the salt bath nearest the reactor outlet; HS top=hot spot temperature of the catalyst nearest the reactor inlet; HS bottom=hot spot temperature of the catalyst nearest the reactor outlet; PHDE or xylene content=phthalide or xylene content of the crude product gas after the finishing reactor, based on phthalic anhydride; PA yield=PA yield in % by weight based on 100%-pure xylene from the analysis of the crude product gas after the finishing reactor.

| Bed | Day [d] | SBT top/ SBT bottom [° C.] | HS top [° C.] | HS bottom [° C.] | Temperature difference [° C.] | PA yield [m/m %] |
|---|---|---|---|---|---|---|
| Comparison 170/130 | 100 | 348/348 | 434 | 366 | 68 | 113.1 |
| | 150 | 348/348 | 434 | 375 | 57 | 112.9 |
| | 200 | 348/348 | 421 | 390 | 31 | 112.0 |
| | 250 | 348/348 | 419 | 394 | 25 | 111.3 |
| According to the present invention 230/70 | 100 | 348/348 | 430 | 362 | 68 | 113.3 |
| | 150 | 348/348 | 431 | 363 | 68 | 113.1 |
| | 200 | 348/348 | 425 | 368 | 57 | 112.9 |
| | 250 | 348/348 | 421 | 371 | 50 | 112.7 |

2b) Preparation of PA—According to the Present Invention (Temperature Variation and Temperature Structuring)

For the catalyst combination operated as comparative experiment in 2a), a temperature difference of >40° C. was set after operation for 250 days by means of temperature structuring (SBT bottom decreased or SBT top increased) or temperature variation (SBT bottom and top increased). All other experimental conditions ere not changed from those in Experiment 2a).

The data listed in the following table were obtained in this experiment (day=day of operation starting from the first start-up of the catalyst; SBT top=salt bath temperature of the salt bath nearest the reactor inlet; SBT bottom=salt bath temperature of the salt bath nearest the reactor outlet; HS top=hot spot temperature of the catalyst nearest the reactor inlet; HS bottom=hot spot temperature of the catalyst nearest the reactor outlet; PHDE or xylene content=phthalide or xylene content of the crude product gas after the finishing reactor, based on phthalic anhydride; PA yield=PA yield in % by weight based on 100%-pure xylene from the analysis of the crude product gas after the finishing reactor.

| Bed 170/130 | Day [d] | SBT top/ SBT bottom [° C.] | HS top [° C.] | HS bottom [° C.] | Temperature difference [° C.] | PA yield [m/m %] |
|---|---|---|---|---|---|---|
| Comparison without temperature structuring | 250 | 348/348 | 419 | 394 | 25 | 111.3 |
| According to the present invention with temperature increase | 252 | 349/349 | 428 | 387 | 41 | 112.3 |
|  | 254 | 350/350 | 437 | 381 | 56 | 112.5 |
| According to the present invention with temperature structuring | 256 | 349/348 | 429 | 385 | 44 | 112.5 |
|  | 258 | 350/348 | 438 | 379 | 58 | 112.8 |
|  | 260 | 348/343 | 419 | 381 | 38 | 112.0 |
|  | 262 | 348/338 | 418 | 370 | 48 | 112.9 |
|  | 264 | 348/335 | 419 | 365 | 54 | 113.1 |

The results reported under 2a) show that the PA yield correlates with the hot spot temperature difference, i.e. under operating conditions relevant to practice, PA is obtained in a higher yield when the temperature difference is above 52° C.

The results reported under 2b) show that when the hot spot temperature difference is too small, increasing the salt bath temperature top and bottom simultaneously and slightly or reducing the temperature of the lower salt bath by keeping the temperature of the upper salt bath constant is sufficient to increase the hot spot temperature difference to more than 52° C.

We claim:

1. A process for preparing phthalic anhydride by gas-phase oxidation of xylene, naphthalene or mixtures thereof over two different fixed-bed catalysts arranged in zones in a shell-and-tube reactor which is thermostated by means of a heat transfer medium, wherein the maximum temperature in the second catalyst zone in the flow direction is at least 52° C. lower than the maximum temperature in the first catalyst zone.

2. A process as claimed in claim 1, wherein the maximum temperature in the second catalyst zone is at least 55° C. lower than that in the first catalyst zone.

3. A process as claimed in claim 1, wherein the maximum temperature in the second catalyst zone is at least 60° C. lower than that in the first catalyst zone.

4. A process as claimed in claim 1, wherein the temperature difference between the maximum temperature in the first and second catalyst zones is controlled via the bed length ratio of the catalyst zones.

5. A process as claimed in claim 4, wherein the bed length of the first catalyst zone is more than 60% of the total bed length of the two catalysts.

6. A process as claimed in claim 4, wherein the bed length of the first catalyst zone is more than 75% of the total bed length of the two catalysts.

7. A process as claimed in claim 1, wherein the temperature difference between the maximum temperature in the first and second catalyst zones is controlled via the temperature of the heat transfer medium.

8. A process as claimed in claim 1, wherein the maximum temperature in the first catalyst zone is less than 470° C.

9. A process as claimed in claim 1, wherein a gas phase having a loading of from 80 to 140 g of o-xylene and/or naphthalene per standard $m^3$ of gas phase is used.

10. A process as claimed in claim 1, wherein the temperature of the heat transfer medium is $\leq 360°$ C.

11. A process as claimed in claim 1, wherein the space velocity of the gas mixture is $\geq 2000$ $h^{-1}$.

* * * * *